(12) United States Patent
Fennhoff et al.

(10) Patent No.: US 6,307,111 B1
(45) Date of Patent: *Oct. 23, 2001

(54) METHOD FOR CONTINUOUS PRODUCTION OF DIHYDROXYDIARYLALKANES

(75) Inventors: Gerhard Fennhoff, Willich; Hans-Josef Buysch; Gerd Fengler, both of Krefeld, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/423,702

(22) PCT Filed: May 5, 1998

(86) PCT No.: PCT/EP98/02643

§ 371 Date: Nov. 12, 1999

§ 102(e) Date: Nov. 12, 1999

(87) PCT Pub. No.: WO98/52895

PCT Pub. Date: Nov. 26, 1998

(30) Foreign Application Priority Data

May 16, 1997 (DE) .............................. 197 20 539

(51) Int. Cl.$^7$ .................................. C07C 39/16
(52) U.S. Cl. .................... 568/728; 568/727; 568/724; 568/749
(58) Field of Search .................. 568/727, 724, 568/749, 728

(56) References Cited

U.S. PATENT DOCUMENTS

| | | | |
|---|---|---|---|
| 2,497,503 | 2/1950 | Jones | 260/621 |
| 2,775,620 | 12/1956 | Williamson | 260/619 |
| 3,242,219 | 3/1966 | Farnham et al. | 260/619 |
| 3,466,337 | 9/1969 | Smith et al. | 260/621 |
| 4,131,749 | 12/1978 | Kiedik et al. | 568/781 |
| 4,209,646 | 6/1980 | Gac et al. | 568/724 |
| 4,277,628 | 7/1981 | Carnahan | 568/749 |
| 4,308,405 | 12/1981 | Kwantes | 568/727 |
| 4,400,555 * | 8/1983 | Mendiratta | 568/728 |
| 4,594,459 | 6/1986 | Inoue | 568/781 |
| 4,859,803 | 8/1989 | Shaw | 568/727 |
| 4,876,391 | 10/1989 | Kissinger | 568/724 |
| 4,906,789 | 3/1990 | Grzywa et al. | 568/727 |
| 4,935,553 * | 6/1990 | Iimuro | 568/727 |
| 4,954,661 | 9/1990 | Iimuro et al. | 568/727 |
| 5,198,591 * | 3/1993 | Kiedik | 568/727 |
| 5,300,702 | 4/1994 | Perkins et al. | 568/724 |
| 5,315,042 | 5/1994 | Cipullo et al. | 568/727 |
| 5,430,199 * | 7/1995 | Caruso | 568/724 |
| 5,504,251 * | 4/1996 | Dyckman | 568/754 |
| 5,672,774 * | 9/1997 | Dyckman | 568/749 |
| 5,783,733 * | 7/1998 | Kissinger | 568/724 |
| 6,025,530 * | 2/2000 | Dyckman | 568/754 |

FOREIGN PATENT DOCUMENTS

| | | |
|---|---|---|
| 0 017 852 | 10/1983 | (EP) . |
| 0 552 518 | 9/1995 | (EP) . |
| 0 630 878 | 3/1998 | (EP) . |

OTHER PUBLICATIONS

Ullmann's Encyclopedia of Industrial Chemistry, 5th edition, vol. A19, Phenol Derivatives, Editors, Barbara Elvers, Stephen Hawkins, Gail Schulz, pp. 348 to 352,(1993).
Ullmann's Encyclopedia of Industrial Chemistry, 5th edition, vol. B2, Crystallization, Exe. Ed. Wolgang Gerhartz, editors, B. Elvers, M. Ravenscroft, J.F. Rounsaville, Gail Schulz, pp. 3–1 to 3–34,(1993).

* cited by examiner

Primary Examiner—Michael L. Shippen
(74) Attorney, Agent, or Firm—Joseph C. Gil; Aron Preis

(57) ABSTRACT

The present invention relates to a process for the continuous production of dihydroxydiarylalkanes (bisphenols) by the reaction of fresh phenol, phenol and isoalkenylphenol from the decomposition of by-products, and ketone. In this process the bulk of the bisphenol is recovered from the reaction mixture by crystallization and the mother liquor obtained is freed from phenol by distillation. The phenol is returned to the reaction and the bottoms obtained during the distillation are decomposed in a reactive rectification after addition of a basic catalyst. The phenol and isoalkenylphenol leaving at the top are led back into the reaction; the bottoms from the first reactive column are acidified and in a second reactive rectification, in the presence of an acid catalyst, are further decomposed into phenol, which distils off and is reused in the reaction, and bottoms, which are disposed of.

1 Claim, 1 Drawing Sheet

METHOD FOR CONTINUOUS PRODUCTION OF DIHYDROXYDIARYLALKANES

Figure 1:
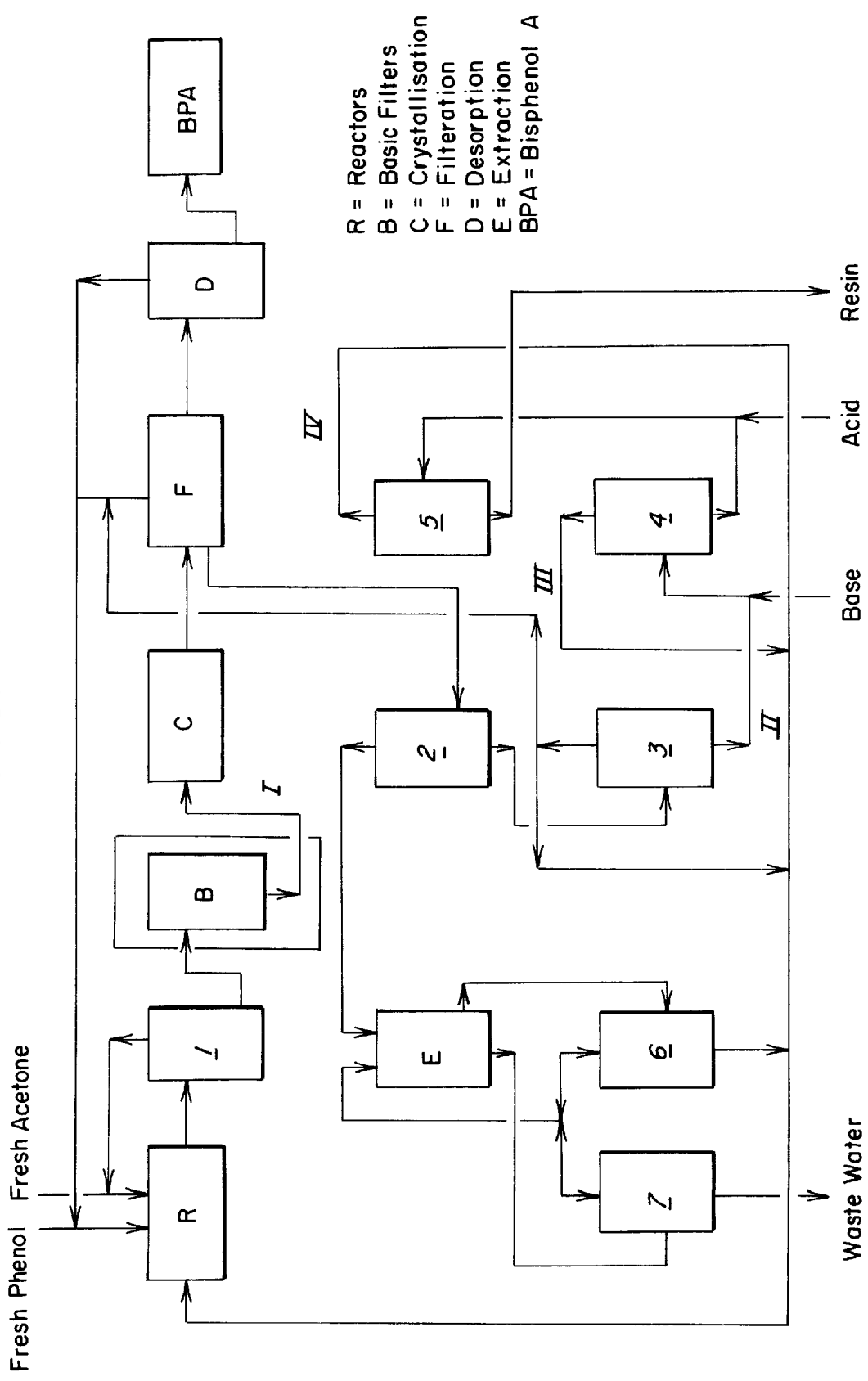

The present invention relates to a process for the continuous production of dihydroxydiarylalkanes (bisphenols) by the reaction of fresh phenol, phenol and isoalkenylphenol from the decomposition of by-products, and ketone. In this process the bulk of the bisphenol is recovered from the reaction mixture by crystallisation and the mother liquor obtained is freed from phenol by distillation. The phenol is returned to the reaction and the bottoms obtained during the distillation are decomposed in a reactive rectification after addition of a basic catalyst. The phenol and isoalkenylphenol leaving at the top are led back into the reaction; the bottoms from the first reactive column are acidified and in a second reactive rectification, in the presence of an acid catalyst, are further decomposed into phenol, which distils off and is reused in the reaction, and bottoms, which are disposed of.

The production of bisphenols by the-acid-catalysed reaction of ketones with phenol is known. There have been a number of different proposals for this (cf., for example, U.S. Pat. Nos. 2,775,620, EP-A 342 758, EP-A 616 993, DE-OS 3 833 900, 4,308,404, 4,308,405, EP-A 630 878, U.S. Pat. Nos. 4,876,391, 3,242,219).

There is a survey of the older literature on bisphenol production in Ullmann's Encyclopedia of Indust. Chem., 5th. Edition, Vol. A 19, pages 348–52. As a rule bisphenols, especially bisphenol A (BPA), industrially the most important of the bisphenols, are prepared by introducing ketone and phenol into a recirculated mother liquor obtained from the working up of bisphenol, this mixture is passed through acidic ion exchangers and the conversion to bisphenol takes place. Any ketone which may possibly not have reacted is recovered from the reaction mixture and led back into the reaction. The reaction mixture is cooled, the bisphenol is if necessary allowed to crystallise out as phenol adduct, separated off and washed with phenol. The phenol is separated from the adduct by flash distillation and pure bisphenol is recovered. The mother liquor from the crystallisation is passed through acidic ion exchangers and isomers contained therein undergo rearrangement to form bisphenol. The bisphenol thus formed is separated by crystallisation and the crystallisate obtained is passed to the first crystallisation step. A portion (approximately 10 to 20%) of the mother liquor now obtained is set aside; the bulk is returned to the reaction. Phenol is distilled off from the portion set aside and is returned to the reaction. The residue obtained during the distillation is removed from the process and is used, for example, for the preparation of phenol resin.

In this procedure, which is relatively complicated, the mother liquor is repeatedly passed over the catalyst. In the course of this many isomers and by-products are formed, as well as coloured compounds which have to be carefully removed from bisphenol, which may necessitate a further crystallisation. Secondly, an appreciable quantity of valuable compounds, such as bisphenol and isomers, are lost in the portion which is set aside and ultimately discharged. This removal from the mother liquor is absolutely essential, so as not to allow the quantity of unusable and interfering compounds to become too great.

Attempts have therefore been made to work up and to decompose the discharged portion, in order to recover the valuable materials for use in the production of bisphenol. For this, too, there have been a number of different proposals. By pyrolysis at about 300° C. it is possible to obtain moderate yields of phenol and alkylphenols, which have still to be thoroughly purified (U.S. Pat. No. 2,497,503). A hydrogenation treatment also leads to valuable products, as is disclosed in EP-A 17 852. The decomposition can also be accelerated by acidic and basic compounds. However, only phenol is obtained by using acids such as sulfuric acid or toluenesulfonic acid (U.S. Pat. No. 3,466,337). Basic catalysts, on the other hand, effect a decomposition of the discharged materials into phenol and isoalkenylphenol. Catalysts mentioned are alkali metal compounds, such as NaOH, KOH, NaHCO$_3$, Na acetate, Na hypophosphite, K$_2$CO$_3$, MgO and Al isopropylate (U.S. Pat. Nos. 4,277,628, 4,594,459, 4,131,749). In this procedure, however, only a part of the discharged material is decomposed, and operation is intermittent or semicontinuous. Wholly continuous processes are unknown.

These processes have been improved, as regards a higher purity of the bisphenol, in that the phenol/isoalkenylphenol mixture from the decomposition is introduced into the first mother liquor after the separation of the first bisphenol portion. The mixture is passed over the acid catalyst and the reaction of isoalkenylphenol with phenol and the rearrangement are allowed to proceed simultaneously. The second bisphenol portion is then separated from the mixture by crystallisation and the second mother liquor is again removed for decomposition. The second bisphenol portion is introduced into the first crystallisation. The purity of the bisphenol is thereby somewhat increased, but the process is rendered more complicated by an additional circulation (U.S. Pat. No. 4,954,661).

It has also been proposed that the second mother liquor in the bisphenol process described above, or the first mother liquor after separation of the first quantity of bisphenol and after the rearrangement, be at least partly worked up by distillation, in order better to utilise the valuable products contained therein. The bisphenol thus obtained is reintroduced into the first crystallisation step and purified there. The low-boiling components containing isomers are introduced into the reaction (WO 94/20445 and EP-A 552 518). The difficulty lies in obtaining at justifiable expense from the mother liquor, which is highly enriched by isomers and by-products, sufficiently pure fractions particularly low in chromans and indans, which are difficult to remove, without excessively increasing the no longer usable residue and diminishing the yield. Because of this, a portion of the distillation products have to be discarded.

The fractions low in bisphenol which are obtained during the distillation may also be decomposed and the decomposition products reintroduced into the process (EP-A 332 203).

It has now been found that an excellent yield of bisphenol of high purity is obtained by a simple, wholly continuous process, if phenol is reacted with ketone and with isoalkenylphenol from the decomposition in such a way that as small a quantity as possible of isomers and by-products is formed, unreacted ketone is distilled off from the reaction mixture, acidic components are optionally separated off, the bulk of the bisphenol contained therein is isolated by crystallisation, the mother liquor and the washing phenol from this crystallisation step are combined, phenol is distilled off and introduced into the reaction, the bottoms are mixed with a basic catalyst and, in a first reactive rectification, are decomposed into phenol and isoalkenylphenol leaving at the top, both of which flow into the reaction, the bottoms obtained during the reactive rectification are acidified and, in the presence of an acid catalyst, in a second reactive rectification are decomposed into phenol, which is introduced into the reaction, and a residue, which is to be disposed of.

Suitable aromatic hydroxyl compounds for the process according to the invention are not substituted in the para position and contain no substituents of the second order, such as cyano groups, carboxyl groups or nitro groups; examples which may be mentioned are phenol, o- and m-cresol, 2,6-dimethylphenol, o-tert.-butylphenol, 2-methyl 6-tert.-butylphenol, o-cyclohexylphenol, o-phenylphenol, o-isopropylphenol, 2-methyl-6-cyclopentylphenol, o- and m-chlorophenol, 2,3,6-trimethylphenol. Preferred compounds are phenol, o- and m-cresol, 2,6-dimethylphenol, o-tert.-butylphenol and o-phenylphenol; phenol is particularly preferred.

Suitable ketones contain at least one aliphatic group on the carbonyl function; examples which may be mentioned are acetone, methyl ethyl ketone, methyl propyl ketone, methyl isopropyl ketone, diethyl ketone, acetophenone, cyclohexanone, cyclopentanone, methyl-, dimethyl- and trimethylcyclohexanone, which may also have geminal methyl groups, such as 3,3-dimethyl-5-methylcyclohexanone (hydroisophorone). Preferred compounds are acetone, acetophenone, cyclohexanone and its homologues containing methyl groups; acetone is particularly preferred. Suitable catalysts for the basic decomposition are those mentioned in the literature, preferably alkali metal oxides and hydroxides, particularly preferably NaOH and KOH. In the process according to the invention, they are introduced into the melt of the decomposition educts, dissolved and homogeneously distributed, the temperature expediently being between 100° C. and 200° C., preferably 120° C. and 180° C.

Suitable catalysts for the acid decomposition are those mentioned in the literature, preferably sulfuric acid, phosphoric acid, phosphorous acid, the partial salts thereof, such as $NH_4HSO_4$, $NaHSO_4$, $KHSO_4$, $NaH_2PO_4$, $KH_2PO_4$, $NH_4H_2PO_4$, $NH_4H_2PO_3$, $KH_2PO_3$ and analogues, also the organic derivatives of these acids, namely aromatic sulfonic acids and disulfonic acids, such as benzenesulfonic acid, toluenesulfonic acid, xylenesulfonic acid, phenolsulfonic acid, diphenyldisulfonic acid, diphenyl ether disulfonic acid, then aromatic phosphonic and phosphinic acids, such as benzene-, toluene- xylenephosphonic and -phosphinic acids, diphenyldiphosphonic acid and diphenyldiphosphinic acid, also solid acids, such as acidic aluminium oxides, aluminas such as bentonites and montmorillonites, zeolites, titanium oxide and zirconium oxide, niobium oxide and tantalum oxide; acidic aluminas are preferred.

The quantities of catalysts added to the mixture to be decomposed are from 0.01 wt. % to 5 wt. %, preferably from 0.05 to 3 wt. %, particularly preferably from 0.1 to 2 wt. %, based on the quantity of decomposed mixture. To render adherence to these specified quantities possible in the case of acid catalysts, after the basic decomposition the basic catalysts must either be removed from the bottoms, which in any event would probably be too expensive, or they must first be neutralised by a strong acid, before the addition of the required quantity of acid catalyst takes place. In this way the presence of sufficient quantities of active acid is ensured. For the purpose of the invention, acidification therefore means that acid is added to the bottoms from the basic decomposition in a quantity such that both the basic catalyst contained therein is neutralised and over and above this there is available a sufficient quantity of acid catalyst for the subsequent acidic decomposition.

The catalysts, for example, dissolved or suspended in phenol, may be metered continuously into the stream flowing in the column where decomposition takes place. But it is also possible, in intermediate containers, to admix them in batches to the material to be decomposed and then to convey this mixture continuously into the column where decomposition takes place.

The columns in which the reactive rectifications are carried out correspond to the distillation columns generally used. In the columns, the decomposition takes place beneath the separation by distillation and fractionation of the decomposition products phenol and isoalkenylphenol from the undecomposed or perhaps undecomposable compounds. In the course of this the decomposition products, generally already sufficiently pure for further use, leave at the top. The undecomposable constituents are discharged as bottoms. Reactive rectifications are known to the person skilled in the art and are described, for example, in Ullmann's Encyclopedia of Industrial Chemistry, 5th. Edition, Vol. B 4, pages 321–8.

In the present case it may be advantageous to decrease the column diameter appropriately in the lower part of the columns where decomposition takes place, to correspond to the decreasing volume of liquid and gas from top to bottom in the column during the decomposition. In order to establish a suitable residence time in the column for the material being decomposed, it is useful to insert trays into the columns where decomposition takes place. This applies particularly to the part in which the decomposition proceeds. In the upper part, the use of filler material or packings may be advisable for an effective separation of the products. In the event that the purity of the phenol distilling off from the second decomposition column is inadequate for use in the bisphenol synthesis, it may be passed into an additional column or else into the first decomposition column and further purified there. Preferred procedures for the reaction to form bisphenol are those which deliver bisphenol at the highest selectivity possible. They are distinguished in that the reaction is carried out at the lowest possible ketone concentration. This can be achieved by reacting phenol with ketone and isoalkenylphenol in at least two serially connected reactors containing acidic ion exchangers and operated at as low a temperature as possible, but with increasing temperatures in the direction of the progressing reaction, the total quantity of ketone and isoalkenylphenol being apportioned between the individual reactors and being distributed homogeneously in the reaction mixture before the introduction into the respective reactors. The selectivity for bisphenol can be further increased if the distribution of ketone and isoalkenylphenol is controlled in such a way that the proportion of the total quantity per reactor is the smaller, the more elevated the temperature of the respective reactor, and the series of reactors is operated within a temperature span of at most 35° C. to 85° C., preferably of 38° C. to 75° C.

It is useful to provide mixing units of known type in front of the individual reactors, in order to ensure the homogeneous distribution of ketone and isoalkenylphenol in the starting phenol and reaction mixture respectively, as well as heat exchangers for the required tempering of the mixture before the passage through the catalyst bed.

After it has left the last reactor of the series and after separation of unreacted ketone, the reaction product is optionally freed from acidic components, as described, for example, in U.S. Pat. No. 4,876,391 or EP-A 552 518 and optionally subjected to a fine filtration in order to remove dust from the catalyst and from the apparatus or other solid contaminants. The reaction mixture then flows into a crystalliser, which is conventionally used for the bisphenol synthesis and is known to the person skilled in the art (Ullmann's Encyclopedia of Industrial Chemistry, 5th. Edition, Vol. B 2, pages 3–1 to 3–34; a crystallising process may be found, for example, in U.S. Pat. No. 4,209,646), wherein the bulk of the bisphenol contained therein is crystallised out (in the case of bisphenol A, as adduct with phenol), separated by filtration, for example with a rotary filter, and washed with phenol. The water of reaction and a little phenol is distilled off from the mother liquor combined with the washing phenol; the distilled phenol is separated by extraction in the usual manner. The water is disposed of and the phenol is returned to the reaction. Phenol is now completely distilled off from the mother liquor in a vacuum. The bottoms obtained are mixed with a basic catalyst, metered continuously into a reactive rectification and therein are decomposed at 190° C. to 270° C., preferably at 200° C. to 260° C., particularly preferably at 210° C. to 250° C., and at 15 to 0.5 mbar, preferably 12 to 1 mbar, particularly preferably 10 to 1 mbar. The distillate, consisting of phenol and isoalkenylphenol and its oligomers, is passed to the reaction. The bottoms, after acidification, are metered into a second reactive rectification which is similar to the previous one and therein are decomposed at 150° C. to 260° C., preferably at 160° C. to 250° C., particularly preferably at 170° C. to 240° C. and at the pressures given above, during which phenol distils off. This phenol, which may optionally be further processed through a column, is again introduced into the reaction stream. Bottoms are withdrawn at the foot of the column, and these are removed for disposal.

If the bottom component resulting from the basic decomposition, owing to a relatively small production run in a bisphenol plant, is too small for the economical operation of one column, it is advisable to combine these small quantities from several runs, or to collect the bottoms from one plant to form a larger quantity and then to decompose this in a suitable apparatus.

By means of the process according to the invention, material yields of up to 98% are obtained, provided that the water of reaction unavoidably formed is removed from the material balance from the beginning. In addition, a particularly pure bisphenol is obtained.

The reaction mixtures leaving the series of reactors may contain, prior to the crystallisation, from 10 to 35 wt. %, preferably 12 to 32 wt. % and particularly preferably 14 to 30 wt. %, bisphenol. Should the content be unsuitable for a crystallisation, it can be adjusted by adding or distilling off phenol.

The process according to the invention, compared with the known bisphenol processes, accordingly has the advantage that it produces a very pure bisphenol in excellent yield in a far simpler and wholly continuous operation.

EXAMPLE (cf. FIG. 1)

BPA was produced in the following manner in a series of three reactors, which were filled with acidic ion exchange material (SC 102, Bayer AG) containing as cocatalyst 3.6 wt. % dimethylthiazolidine.

5438 parts by weight per hour of phenol, together with one third per hour of a quantity of 274 parts by weight of fresh acetone and 402 parts by weight of decomposition product containing phenol and isopropenylphenol, with a loading of 0.6 kg/l catalyst per hour, were conveyed into the first reactor at 50° C. The resulting reaction product was mixed with an additional one third per hour of the above quantity of acetone and decomposition product, tempered at 60° C. and passed into the second reactor. After leaving the second reactor, the last one third per hour of the above quantity of acetone and decomposition product was mixed into the reaction product, tempered at 70° C. and fed into the third reactor. The loading rate was maintained at 0.6 kg/l×h for all the reactors. The acetone conversion was 97% to 98%.

This continuously operated apparatus for the production of bisphenol A (BPA) by the reaction, catalysed by acidic ion exchangers, of fresh phenol, phenol from basic and acidic decomposition, acetone and isopropenylphenol from alkaline decomposition, yielded 6114 parts by weight per hour of reaction mixture having the composition I shown in Table 1, after the removal by distillation of residues of unreacted acetone (1) and optionally a filtration though a filter and basic ion exchanger (B) for the removal of acids leached out of the acidic ion exchanger.

By working up the reaction mixture in the conventional manner by crystallisation (C), suction filtration, washing with phenol and pressing (F), a BPA-phenol adduct was obtained which, after flash distillation of the phenol in the vacuum (D), yielded 983 parts by weight per hour BPA having a purity of 99.78%. The mother liquor and washing phenol accumulating during the process were continuously evaporated in a vacuum (2,3); the phenol distilled off, after extraction (E) and separation of water and extracting agents (6,7), was readded partly to the reaction and partly to the washing stage; the high-boiling residue, after 0.5 wt. % KOH had been homogeneously distributed therein, was metered as melt II at a rate of 425 parts by weight per hour into a reactive rectification column having 20 trays (4), at an overhead temperature of 80° C. to 82° C. and a temperature of 238° C. at the bottom and operated at 2 mbar. Distillate having the composition III distilled over from this reactive column at a rate of 376 parts by weight per hour and flowed back into the reaction to produce BPA. Residue was discharged from the bottom of the column at a rate of 48 parts by weight per hour. 2 mol toluenesulfonic acid per mol of contained KOH was added to this melted residue, which was then passed continuously into a reactive rectification column (5) likewise having 20 trays, which was operated at an overhead temperature of approx. 73° C. to 76° C. and a temperature of approx. 205° C. at the bottom and at a pressure of 5 mbar.

55 wt. % of the material introduced distilled over from this second reactive column as distillate having the composition IV and 45 wt. % was discharged from the bottom as waste to be disposed of.

In the production of 983 parts by weight of BPA, 22 parts by weight of waste was therefore obtained, which corresponds to a material yield of 97.8% (after prior withdrawal of the water from the condensation of acetone and phenol).

TABLE 1

|   | o,o-'BP | o,p-'BP | Chrom. | BPA | Ind. | Tri-sph. | MG 402 | NP | Σ IPENP | Phenol | Parts by wt/h |
|---|---|---|---|---|---|---|---|---|---|---|---|
| I | 0.09 | 5.06 | 0.22 | 93.72 | 0.16 | 0.60 | 0 | 0.14 | 0 | 0 | 6114 |
| II | 0.19 | 16.10 | 0.51 | 75.76 | 020 | 2.10 | 0 | 1.22 | 0 | 3.91 | 425 |
| III | 0.02 | 0.05 | 0.06 | 0.38 | 0.01 | 0.01 | 0 | 0.01 | 52.01 | 47.32 | 376 |
| IV | 0.01 | 0.03 | 0.20 | 0.11 | 0.13 | 0 | 0 | 0.24 | 0 | 99.3 | 26 |

What is claimed is:

1. A continuous process for producing dihydroxydiarylalkane in a series of at least two reactors comprising
   (i) reacting phenol with at least some ketone and at least some isoalkenylphenol at the lowest possible temperature in a first reactor to form a reaction mixture and continuing the reaction at increasing temperatures in the succeeding at least one reactor and introducing at least portions of the remaining ketone and isoalkenylphenol in said at least one succeeding reactor to form at least one succeeding reaction mixture, and
   (ii) distilling off and removing unreacted ketone from the reaction mixture, and
   (iii) separating dihydroxydiarylalkane from the reaction mixture by crystallization to obtain mother liquor and crystals and washing the crystals thus obtained with washing phenol, and
   (iv) combining the mother liquor with said washing phenol, distilling off the phenol and returning said phenol to the reaction, and
   (v) decomposing the bottoms which include dihydroxydiarylalkane, isomers in the presence of a catalytic quantity of base in a first reactive rectification to produce (a) phenol and isoalkenylphenol distillate which leave at the top and (b) high boiling residue at the bottom, and
   (vi) acidifying said high boiling residue so that it contains a catalytic quantity of acid, and decomposing said residue in a second reactive rectification to produce (c) phenol and (d) bottoms, and
   (vii) returning the phenol produced in (vi) and the distillate produced in (v) to the reaction to produce dihydroxydiarylalkane.

* * * * *